(12) United States Patent
Zhang et al.

(10) Patent No.: US 10,465,157 B2
(45) Date of Patent: Nov. 5, 2019

(54) SYSTEMS AND METHODS FOR ASEPTIC SAMPLING

(71) Applicant: General Electric Company, Schenectady, NY (US)

(72) Inventors: Chengkun Zhang, Rexford, NY (US); Kenneth Roger Conway, Clifton Park, NY (US); Donald Joseph Buckley, Schenectady, NY (US); Eugene Pauling Boden, Scotia, NY (US); Weston Blaine Griffin, Niskayuna, NY (US); Anshika Bajaj, Niskayuna, NY (US); Reginald Donovan Smith, Schenectady, NY (US); Zhipeng Zhang, Cupertino, CA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 258 days.

(21) Appl. No.: 14/462,594

(22) Filed: Aug. 19, 2014

(65) Prior Publication Data

US 2016/0053296 A1 Feb. 25, 2016

(51) Int. Cl.
*C12M 1/00* (2006.01)
*G01N 1/18* (2006.01)
(Continued)

(52) U.S. Cl.
CPC .............. *C12M 23/40* (2013.01); *B01L 3/561* (2013.01); *C12M 33/06* (2013.01); *C12M 37/02* (2013.01); *G01N 1/18* (2013.01); *B01L 2200/141* (2013.01)

(58) Field of Classification Search
CPC ......... G01N 1/18; C12M 33/06; C12M 23/40; B01L 3/56; B01L 3/561
See application file for complete search history.

(56) References Cited

U.S. PATENT DOCUMENTS 4,047,526 A * 9/1977 Reynolds ................ A61M 1/02
604/406
RE32,056 E * 12/1985 Granzow ............ A61M 39/143
141/1
(Continued)

FOREIGN PATENT DOCUMENTS

DE 3607582 A1 9/1987
JP 61002038 A 1/1986

OTHER PUBLICATIONS

International Search Report and Written Opinion issued in connection with corresponding PCT Application No. PCT/EP2015/067584 dated Nov. 10, 2015.

*Primary Examiner* — Justin N Olamit
(74) *Attorney, Agent, or Firm* — Arent Fox LLP

(57) ABSTRACT

A sampling assembly configured to be coupled to a sample source is provided. The sampling assembly is configured to facilitate aseptic sampling at one or more instances in time. The sampling assembly includes a first conduit having a first port and a second port, where the first port is configured to be coupled to the sample source, and where the second port is configured to be hermetically sealed. The sampling assembly further includes a plurality of sub-conduits having corresponding sub-ports, where each of the plurality of sub-conduits is operatively coupled to the first conduit at respective connection points, and where each of the sub-ports is in fluidic communication with the first conduit. Moreover, the sampling assembly includes a plurality of sampling kits, where each sampling kit of the plurality of sampling kits is operatively connected to a respective sub-port of a corresponding sub-conduit.

18 Claims, 7 Drawing Sheets

(51) Int. Cl.
    *B01L 3/00*        (2006.01)
    *C12M 1/32*      (2006.01)
    *C12M 1/12*      (2006.01)

(56) References Cited

U.S. PATENT DOCUMENTS

| | | | |
|---|---|---|---|
| 4,829,002 A * | 5/1989 | Pattillo | C12M 23/14 |
| | | | 141/244 |
| 4,999,307 A * | 3/1991 | Oakley | C12M 33/06 |
| | | | 435/309.1 |
| 7,052,603 B2 | 5/2006 | Schick | |
| 7,601,545 B2 | 10/2009 | Barringer | |
| 7,906,323 B2 | 3/2011 | Cannon et al. | |
| 8,281,672 B2 * | 10/2012 | Lee | C12M 37/02 |
| | | | 73/863 |
| 8,640,556 B2 | 2/2014 | Hofman | |
| 8,685,746 B2 | 4/2014 | Halverson et al. | |
| 8,701,506 B2 | 4/2014 | Morris | |
| 9,068,157 B2 * | 6/2015 | Bruecher | C12M 33/04 |
| 9,677,975 B2 | 6/2017 | Zhang et al. | |
| 9,707,326 B2 * | 7/2017 | Muller | A61M 1/3496 |
| 2004/0009542 A1 * | 1/2004 | Dumont | A61J 1/10 |
| | | | 435/7.32 |
| 2005/0074872 A1 * | 4/2005 | Furino | B01L 3/0241 |
| | | | 435/288.4 |
| 2006/0039833 A1 | 2/2006 | Yong | |
| 2007/0088216 A1 | 4/2007 | Pfeiffer et al. | |
| 2010/0236340 A1 | 9/2010 | Lee et al. | |
| 2011/0079095 A1 | 4/2011 | Bruecher | |
| 2011/0201100 A1 | 8/2011 | Proulx et al. | |
| 2012/0297900 A1 | 11/2012 | Intelisano | |
| 2016/0123848 A1 | 5/2016 | Griffin et al. | |

* cited by examiner

SYSTEMS AND METHODS FOR ASEPTIC SAMPLING

BACKGROUND

Embodiments of the present specification relate to aseptic sampling, and more particularly to aseptic sampling at one or more instances in time.

Typically, in a cell culture process, growth media is used to nourish cells and carry away cell-secreted products. The growth media is provided continuously or intermittently to a culture vessel for in vitro culture of biological cells for: (1) recovery of cell-secreted proteins from the culture vessel, and/or (2) other purposes, such as expansion of cells. Further, the growth media is provided to the culture vessel via a flow path that is formed using suitable tubing. Often, this tubing is present as a closed system, where the closed system includes provisions for periodic or continuous replenishment of the growth media by adding fresh growth media.

It is often desirable to monitor the cell culture process. Further, monitoring of the growth media in the culture vessel and/or at one or more points in the flow path is an effective way of monitoring and/or controlling the cell culture process. Typically, monitoring is performed by installing sensors in the culture vessel, as well as periodically drawing a portion of the growth media or a sample having a mix of cells and the culture media from the culture vessel for analysis. Thus, for example, analysis of the growth media before, during, and after passage through the culture vessel for monitoring one or more process conditions, such as nutrient components, cell-secreted proteins, cell-secreted metabolites, or the like may provide significant information regarding one or more of a number of viable cells in the culture vessel, a rate of nutrient consumption by the cells, a rate of product secretion, cell growth rates, stages of cell growth, presence or absence of subdivision of cells, and the like. Such information may be used to monitor the system and/or to indicate changes that may require alteration of the process conditions, the composition of the growth media, or the like to optimize the cell culture process.

Further, it is required for the cell culture process to be carried out under aseptic conditions as in the absence of the aseptic conditions the cells may be contaminated thereby resulting in contamination of products recovered therefrom and/or loss of cell viability. As a consequence, in vitro animal cell culture systems and their component parts are initiated and maintained under sterile conditions, with each portion or the entirety of the system being sterilized prior to commencement of the process, and using sterile culture medium and uncontaminated seed cell stocks.

However, during sampling there is a need to insure that sampling of the culture media or the sample is carried out in a manner so as to avoid introduction of contaminants into the pre-established sterile system. Conventional techniques for accomplishing this sterile withdrawal of the sample are elaborate, expensive, and time consuming. By way of example, in some of the existing systems, the area from which the sample is to be drawn, be it the culture vessel or the flow path to or from the culture vessel, is provided with a sample port such as in the form of a short segment of tubing or other appropriate structures. The system is then invaded via this sample port to withdraw a desirable quantity of the sample. Typically, sensors are deployed in and around the culture vessel to monitor the various parameters in the bioreactor. Further, a portion of inoculum, which is a mixture of the cells and the growth medium, is drawn from the culture vessel at different instances in time to monitor the cell culture process that is taking place in the culture vessel.

Each sampling instance requires drawing a portion of the sample from the culture vessel. Different tubes are attached to the ports or are passed through the ports of the culture vessel at different instances in time for different sampling instances. Any leakage or contamination in the tubing or in the connection between the culture vessel and the tubing may introduce contamination in the culture vessel. Additionally, every sampling instance is accompanied by a user attaching some sort of tubing either directly or indirectly to the culture vessel, thereby increasing the risk of contamination of the inoculum. By way of example, a plastic sampling bag or a syringe may be attached to the tubing to collect the sample that is drawn from the culture vessel. In addition to the increased risk of introduction of the contaminants due to coupling of the sampling bags/syringes to the culture vessel, there is also a likelihood of a portion of the sample being left in the tubing after the sampling instance. This residual sample may then be inadvertently carried over to the next sampling instance, thereby jeopardizing the purity of the sample obtained in the next sampling instance. Further, each sampling instance increases the likelihood of contamination of the inoculum.

Hence, it is desirable to insure that sampling of the growth medium or culture fluid be carried out in a manner which avoids introduction of contaminants into the pre-established sterile system.

Consequently, in addition to the complex nature and risk of contamination associated with known sampling techniques, there also may exist an inherent limitation on the number or frequency of samplings which may be accommodated, either by reason of a limited number of sterilizable sequences to which a particular connector can be subjected to before severe degradation occurs or simply by reason of the inordinate amount of time needed to perform a sample withdrawal. These limitations may pose significant problems in situations where rapid and frequent sampling is required in order to monitor a potentially fast-changing situation. Still further, of course, elaborate and/or time-consuming sampling techniques can add significantly to the overall cost of the culture process.

BRIEF DESCRIPTION

In accordance with aspects of the present specification, a sampling assembly configured to be coupled to a sample source is provided. The sampling assembly is configured to enable aseptic sampling at one or more instances in time. The sampling assembly includes a first conduit having a first port and a second port, where the first port is configured to be coupled to the sample source, and where the second port is configured to be hermetically sealed. The sampling assembly further includes a plurality of sub-conduits having corresponding sub-ports, where each of the plurality of sub-conduits is operatively coupled to the first conduit at respective connection points, and where each of the sub-ports is in fluidic communication with the first conduit. Moreover, the sampling assembly includes a plurality of sampling kits, where each sampling kit of the plurality of sampling kits is operatively connected to a respective sub-port of a corresponding sub-conduit.

In accordance with another aspect of the present specification, a sampling system configured to enable aseptic sampling at one or more instances in time is provided. The sampling system includes a sample source configured to house a biological inoculum or inoculum mixture and a sampling assembly operatively coupled to the sample source. Further, the sampling assembly includes a first conduit having a first port and a second port, where the first port is configured to be coupled to the sample source, and where the second port is configured to be hermetically sealed. The sampling assembly further includes a plurality of sub-conduits having corresponding sub-ports, where each of the plurality of sub-conduits is operatively coupled to the first conduit at respective connection points, and where each of the sub-ports is in fluidic communication with the first conduit. Moreover, the sampling assembly includes a plurality of sampling kits, where each sampling kit of the plurality of sampling kits is operatively connected to a respective sub-port of a corresponding sub-conduit.

In accordance with yet another aspect of the present specification, a method for aseptic sampling at one or more instances in time is provided. The method includes providing a sample source and providing a sampling assembly. The sampling assembly includes first conduit having a first port and a second port, where the first port is configured to be coupled to the sample source, and where the second port is configured to be hermetically sealed. The sampling assembly further includes a plurality of sub-conduits having corresponding sub-ports, where each of the plurality of sub-conduits is operatively coupled to the first conduit at respective connection points, and where each of the sub-ports is in fluidic communication with the first conduit. Moreover, the sampling assembly includes a plurality of sampling kits, where each sampling kit of the plurality of sampling kits is operatively connected to a respective sub-port of a corresponding sub-conduit. Further, the method includes coupling the first port of the first conduit to the sample source to provide a fluidic communication between the sample source and at least a portion of the fluid conduit. Moreover, the method includes adjusting one or more first flow controllers to allow a portion of the sample to flow out of the sample source and into the first conduit and a portion of a corresponding sub-conduit of the plurality of sub-conduits. Additionally, the method includes providing a negative pressure in a sampling kit of the plurality of sampling kits to enable a flow of the portion of the sample from the sample source and the corresponding sub-conduit into the sampling kit. Further, the method includes drawing the portion of the sample from the sample source and the corresponding sub-conduit in the sampling kit.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
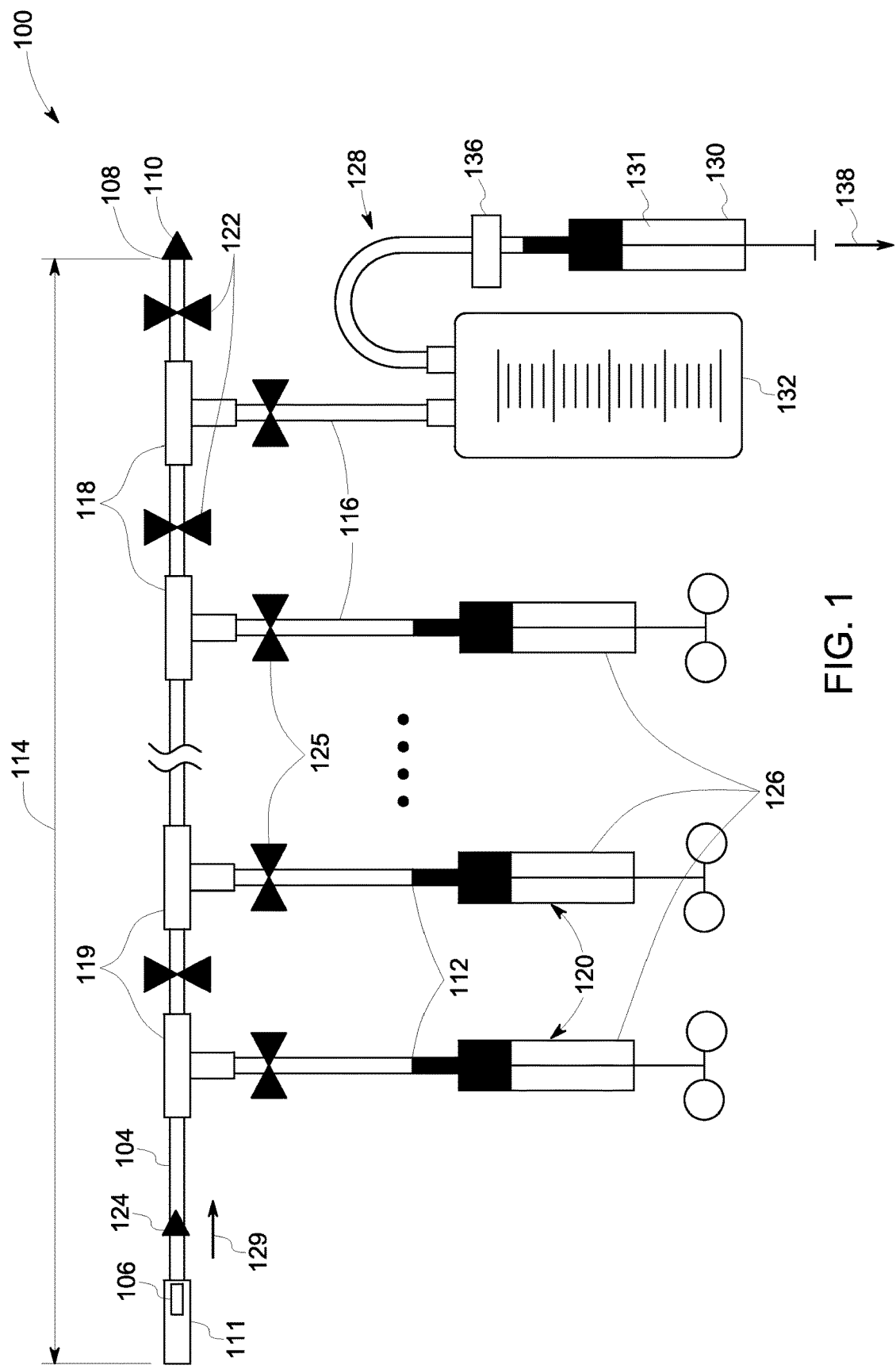
FIG. 1 is a schematic representation of a sampling assembly configured to aseptically draw one or more samples from a sample source, in accordance with aspects of the present specification.

Embodiments of the present specification relate to sampling assemblies, sampling systems and sampling methods for aseptic sampling or drawing samples from a sample source at one or more instances in time. Further, the step of aseptically drawing the sample may enable drawing the sample from a sample source without introducing any substantial amount of unintended micro-organisms. In one embodiment, the amount of micro-organisms that are below the substantial amount may not be detectable using known detection devices. Advantageously, the sampling assembly is configured to facilitate multiple aseptic sampling instances without carryover of a sample residue from a previous sampling instance to the new sampling instance. In one embodiment, the sampling assembly may be configured to provide provisions for purging at least a portion of the sampling assembly after a sampling instance. The step of purging the portion of the sampling assembly after the sampling instance prevents carryover of a residual sample that is left in a tubing of the sampling assembly from the previous sampling instance to a subsequent sampling instance.

In certain embodiments, a pre-assembled sampling assembly configured to aseptically draw samples from a sample source at different instances in time is provided. The sampling assembly is configured to be coupled to different types of sample sources. The sample source is configured to house and effect production of a protein, biological sample or other cultures of interest. The sampling assembly may be pre-sterilized before coupling the sampling assembly to the sample source. In certain other embodiments, a pre-assembled sampling system having a sampling assembly aseptically coupled to a sample source may be provided.

As will be appreciated, during cell culture of cells a growth medium is used to nourish the cells. It is well known that monitoring of an inoculum at one or more instances in time is useful in monitoring and controlling the cell culture process. To that end, an inoculum including a mixture of the cells and the growth medium is monitored by intermittently withdrawing a small portion of the inoculum for analysis. Since the cell culture occurs over a period of time, sampling of the inoculum may be accomplished by drawing samples at instances separated in time. By way of example, analysis of the inoculum may be used to obtain information corresponding to number of viable cells in a culture vessel, rates of nutrient consumption by the cells and the rate of product secretion, cell growth rates, particular stages of cell growth or subdivision, and the like. It may be noted that monitoring may be performed to obtain information regarding the cell culture, and if required, to indicate a need for a change of one or more process conditions, growth medium composition, growth medium flow rate in the sample source, or the like designed to optimize the cell culture process. The cell culture process is initiated and maintained under sterile conditions, with each portion or the entirety of the system being sterilized prior to commencement of the process, and using sterile growth medium and uncontaminated seed cell stocks.

It may be noted that in case of conventional methods of sampling of the inoculum, there is a possibility of external impurities being introduced in the inoculum. Additionally, when sampling is performed at two or more instances in time, it is likely that a residue from a previous sampling instance is carried over to a next sampling instance. In the cell culture process it is highly desirable to: (1) prevent entry of external impurities in the sample source or associated components, and (2) minimize or prevent carryover of a residual sample from the previous sampling instance to the next sampling instance.

In certain embodiments, the systems and methods for aseptic sampling may include coupling a sampling assembly to a sample source. Further, in certain embodiments, a pre-sterilized sampling assembly may be made available for easy installation. The sampling assembly may be configured to be coupled to different types of sample sources. Advantageously, the sampling assembly enables aseptically sampling at one or more instances in time. Moreover, the sampling assembly facilitates aseptically sampling with zero or minimal carryover of the residual sample from the previous sampling instance into the next sampling instance.

Before describing the present specification in further detail, a number of terms will be defined. Use of these terms does not limit the scope of the invention but only serve to facilitate the description of the embodiments.

As used herein, the singular forms "a," "an," and "the" include plural referents unless the context clearly dictates otherwise.

As used herein the phrase, "biological samples" mean, but are not limited to, any particle(s), substance(s), extract(s), mixture, and/or assembly derived from or corresponding to one or more organisms, cells, and/or viruses. As will be appreciated cells which may be cultured in an automated cell management system include one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other cells capable of being cultured in vitro as known in the art. The biological sample also may include additional components to facilitate analysis, such as fluid (e.g., water), buffer, culture nutrients, salt, other reagents, dyes, etc. Accordingly, the biological sample may include one or more cells disposed in a growth medium and/or another suitable fluid medium.

Further, as used herein, the term "sample" may be used to refer to a growth medium or a mixture of cells and the growth medium.

As used herein, the term "sterile environment" refers to an environment that is substantially free of unintended microorganisms.

Moreover, as used herein, the term "sample source" refers to any suitable apparatus, such as a large fermentation chamber, bioreactor, bioreactor vessel and/or culture vessel, for growing organisms such as bacteria or yeast under controlled conditions for production of substances such as pharmaceuticals, antibodies, or vaccines, or for the bioconversion of organic waste. Further, the term "sample source" includes vessels for both aerobic and anerobic cultivation of microbial, animal, insect and plant cells, and thus encompassing a fermentor.

Further, as used herein, "cell culture" entails growth, maintenance, differentiation, transfection, or propagation of cells, tissues, or their products.

Also, as used herein the phrase "growth medium" or "growth media" means a liquid solution used to provide nutrients (e.g., vitamins, amino acids, essential nutrients, salts, and the like) and properties (e.g., similarity, buffering) to maintain living cells (or living cells in a tissue) and support their growth. Commercially available tissue growth medium is known to those skilled in the art. The phrase, "cell growth medium" as used herein means tissue growth medium that has been incubated with cultured cells in forming a cell culture; and more preferably refers to tissue growth medium that further includes substances secreted, excreted or released by cultured cells, or other compositional and/or physical changes that occur in the medium resulting from culturing the cells in the presence of the tissue growth medium.

Additionally, as used herein, the term "sampling instance" may be used to refer to an event of drawing a sample at a given instance in time.

FIG. 1 illustrates a sampling assembly 100 configured to aseptically draw one or more samples from a sample source (not shown in FIG. 1). Further, the one or more samples may be drawn from the sample source at one or more instances that are separated in time. The sampling assembly 100 includes a first conduit 104 having a first port 106 and a second port 108. In the illustrated embodiment, the first port 106 of the first conduit 104 is configured to be coupled to the sample source. Further, the second port 108 may be configured to be functionally closed. In one example, the second port 108 may be mechanically sealed, clamped, thermally sealed, or combinations thereof. In the illustrated embodiment, the second port 108 is functionally closed using a mechanical stopper 110. The sampling assembly 100 may be pre-sterilized and sealed. By way of example, the first port 106 of the first conduit 104 of the sampling assembly 100 may be temporarily sealed using a sealing plug 111. In another embodiment, the first port 106 of the first conduit 104 may be a closed end. Simply, at the time of use, the sterilized sampling assembly 100 may be coupled to the sample source by removing the sealing plug 111 and forming a sterile connection between the sampling assembly 100 and the sample source. Alternatively, in case of the sealing plug 111, the sampling assembly 100 may be coupled by disengaging a portion of the first conduit 104 near the first port 106, and then coupling the sampling assembly 100 to the sample source. In certain embodiments, the sterilized sampling assembly may be used in conjunction with a cell culture vessel for in vitro culturing of biological cells such as, but not limited to stem cells. The sampling assembly may be used to carry out sampling to allow intermittent sampling and monitoring of the cell culture contained in the assembly or for example for the recovery of cell-secreted proteins or the partial or complete removal or testing of the expansion of cells.

Further, in some embodiments, the first and second ports 106 and 108 may be situated at physical extremities of the first conduit 104 as illustrated in FIG. 1. Alternatively, in some other embodiments, the first and second ports 106 and 108 may be disposed at locations other than the physical extremities of the first conduit 104. Additionally, the sampling assembly 100 includes a plurality of sub-ports 112 disposed along a first dimension (for example, a length) 114 of the first conduit 104. In particular, the sub-ports 112 may be disposed at respective ends of a plurality of sub-conduits 116. Further, the plurality of sub-conduits 116 emanate from spaced-apart areas along the first dimension 114 of the first conduit 104. The sub-conduits 116 may be coupled to the first conduit 104 at corresponding connection junctions 118. The sub-conduits 116 may be in fluidic connection with the first conduit 104. The sub-conduits 116 may be coupled to the first conduit 104 using connectors 119. In one embodiment, the connectors 119 may be hollow T-shaped connectors, Y-shaped connectors, or any other suitably shaped connectors. In one embodiment, the first conduit 104 may be a continuous conduit. Further, the plurality of sub-conduits 116 may emanate from spaced-apart areas along the first dimension 114 of the first conduit 104. Alternatively, in another embodiment, the first conduit 104 may be a combination of interconnected portions of conduits. By way of example, the first conduit 104 may be formed from lengths of interconnected portions of the conduit or tubing that is connected at the connection junctions 118. In one such example embodiment, the sampling assembly 100 may be formed by one or more manifolds that are operatively coupled in fluidic communication with one another. In one embodiment, the manifolds may be made from hollow T-connectors, Y-connectors, or the like.

Moreover, the first conduit 104 may be hermetically sealed at the second port 108. Further, the first port 106 may initially be closed for construction and sterilization of the sampling assembly 100. However, the first port 106 is adapted to be opened for sterile connection and liquid communication with the sample source through which the inoculum may flow out of the sample source in the first conduit 104 for a sampling instance. It may be noted that any suitable number of sub-conduits 116 may be pre-arranged along the first dimension 114 of the first conduit 104 depending upon the envisioned or desirable number of samples that may need to be drawn from the sample source during the cell culture process.

In certain embodiments, the first conduit 104 and the plurality of sub-conduits 116 may be made of poly-vinyl chloride (PVC), polyethylene (PE), or both. however, other polymeric materials may also be employed to form the sub-conduits 116. Liquid-tight and aseptic sealing at the connector junctions 118 may be facilitated by arranging suitable connectors 119 and conduits 104 and 116. Further, the material of the conduits 104 and 116 may be suitable for sterilization processes. In one embodiment, the sampling assembly 100 may be pre-sterilized using sterilization methods, such as, but not limited to, gamma radiation, ethylene oxide (ETO), or both.

In certain embodiments, the sampling assembly 100 may include a plurality of sampling kits generally represented by reference numeral 120. The sampling kits 120 are aseptically coupled to the first conduit 104. In particular, each sampling kit 120 is coupled to a respective sub-port 112 of the plurality of sub-ports 112. It may be noted that shape, size and number of the sampling kits 120 may vary based on sampling requirements. By way of example, the number of sampling kits 120 may be decided based on sampling instances that may be envisioned. Further, it may be noted that the sampling kits 120 may be pre-sterilized before coupling the sampling kits to the sub-ports 112. In one embodiment, the sampling kits 120 may be made of plastic materials with the open sampling end suitably sized and shaped so as to be compatible within the open exit ends or sub-ports 112 of the sub-conduits 116. Further, a liquid-tight and aseptic seal may be achieved between the sampling kits 120 and the sub-conduits 116 through a force-fit. Additionally, the force-fit may be further enhanced by applying a compressive force about the sample conduit tube periphery. Alternatively, a liquid-tight and aseptic seal may be achieved between the sampling kits 120 and the sub-conduits 116 using chemical bonding or mechanical fitting, such as one or more barbs. Further, in some embodiments, a suitable flexible plastic such as nylon film may be used to form a bag-like enclosure about the sampling kit 120 (e.g., a syringe) and its point of connection to the sample conduit tube so as to insure maintenance of sterility when the sampling kit is being manipulated, through the envelope material, to withdraw a liquid sample.

Non-limiting examples of the sampling kits 120 may include a sampling pillow, a sampling syringe, a sampling container, or combinations thereof. Further, it may be noted that some or all of the sampling kits 120 may be same or different. By way of example, in the illustrated embodiment, sampling kits 126 are different from a sampling kit 128. In the illustrated embodiment, the sampling kits 126 include syringes operatively coupled to their respective sampling ports 112 using the respective sub-conduits 116. Further, the sampling kit 128 includes a syringe 130 that is operatively coupled to a sampling container 132. The sampling container 132 in turn is coupled to the respective sampling port 116. In one embodiment, the sampling container 132 is a rigid plastic vessel or bottle that does not collapse substantially when the corresponding syringe 130 is pulled out to draw the sample in the sampling container 132. In one example, the sampling kit 128 may be desirable in instances where it is desirable to draw a larger volume of the sample into the sampling container 132.

Optionally, a filter 136 may be disposed between the syringe 130 and the sampling container 132. The filter 136 may be an air filter that is configured to prevent any impurities from the surrounding environment from entering the sub-conduit 116 or the first conduit 104 and finally, the sample source. By way of example, when the syringe 130 is drawn or pulled back in a direction represented by arrow 138, a barrel 131 of the syringe 130 is exposed to the air present in the surrounding non-sterile environment. In operation, as the syringe 130 is being pulled, a portion of the barrel 131 of the syringe 130 comes in contact with the air in the surrounding non-sterile environment. Advantageously, introducing the filter 136 between the syringe 130 and the sampling container 132 ensures that the sampling container 132 remains sterile and is not exposed to the air of the non-sterile environment.

Moreover, it may be noted that the arrangement of the sampling kits 120 disposed along the length 114 of the first conduit 104 may be in any convenient configuration. By way of example, the various sampling kits 120 may or may not be disposed in an equi-distance configuration along the first conduit 104. Further, the sampling kits 120 may or may not extend in the same direction from the primary conduit 104. Although not illustrated, in an alternative embodiment, the sampling kits 120 may be alternately disposed on opposite sides along the length 114 of the first conduit 104.

In certain embodiments, the sampling assembly 100 may include one or more fluid flow controllers and/or fluid flow regulators designed to facilitate sampling, purging at least a portion of the first conduit 104 and corresponding sub-conduits 116, and preventing the growth medium from returning to the culture vessel. Further, the sampling assembly 100 is configured to enable aseptic sampling of the culture vessel one or more times without substantial carry over contamination from one sampling instance to the next sampling instance.

In the illustrated embodiment, each sub-conduit 116 of the plurality of sub-conduits 116 may be used for a single sampling instance. Further, subsequent to the sampling instance, the respective sub-conduit 116 may be isolated using a corresponding flow controller. In some embodiments, a sealer, such as a mechanical sealer, a thermal sealer, or both may be used to seal the sub-conduit 116 at two or more locations. Subsequently, the sub-conduit 116 may be cut between the two sealed locations on the sub-conduit 116. In a non-limiting example, the sealer may include a bar sealer. It may be noted that cutting the sub-conduit 116 between the two sealed locations enables aseptically decoupling a corresponding sampling kit 120 from the sampling assembly 100. Further, cutting the sub-conduit 116 between the two sealed locations ensures that the distal end of a portion of the sub-conduit 116 that is attached to the first conduit 104 remains hermetically sealed upon separation of the sampling kit 120.

In certain embodiments, samples may be drawn through a particular sub-conduit 116 using a plurality of first flow controllers 122 and a plurality of second flow controllers 125. Additionally, one or more flow regulators 124 may be employed at various locations within the sampling assembly 100. In certain embodiments, one or more first flow controllers 122 may be disposed along the length 114 of the first conduit 104. In particular, the first flow controllers 122 may be disposed between neighboring connector junctions 118. Further, the first flow controllers 122 may be configured to control flow of the sample from the sample source to the sub-conduits 116. In addition, each second flow controller 125 may be disposed between the sampling kits 120 and the first conduit 104. Specifically, one or more second flow controllers 125 may be operatively coupled to each sub-conduit 116 of the plurality of sub-conduits 116. In operation, the sample may be drawn only in a portion of the first conduit 104, where the portion of the first conduit 104 extends between the sample source and a respective sub-conduit 116 that connects the sample source to the corresponding sampling kit 120. Further, in a non-limiting example, one or more samples may be drawn at same or different instances in time using the sampling kits 120 in a sequential order starting from the sampling kit 120 disposed closest to the sample source. However, using the sampling kits 120 in the sequential order may or may not be necessary.

In the illustrated embodiment, the second port 108 of the first conduit 104 is hermetically sealed to maintain a sterile environment in the sampling assembly 100. Non-limiting examples of a hermetic seal may include a mechanical stopper, a clamp, sealing, or combinations thereof. However, alternatively, the second port 108 may be hermetically sealed by other means, such as by fusion (e.g., thermal fusion, chemical fusion, or both). Hermetically sealing the second port 108 of the first conduit 104 prevents impurities from entering the sampling assembly 100 via the second port 108. Further, sealing the second port 108 facilitates transfer of a portion of the sample out of the sample source and into the portion of the length 114 of the first conduit 104 in a sterile environment. Moreover, at the end of a sampling instance, the corresponding sub-conduit 116 is hermetically sealed.

In certain embodiments, the flow regulator 124 may be operatively coupled to the sample source. In the illustrated embodiment, the flow regulator 124 may be disposed between the sample source and the connector junction 118 disposed closest to the sample source. Further, the flow regulator 124 may be operatively coupled to the sample source to enable a flow of at least a portion of the sample from the sample source to one or more sampling kits 120 in a first direction represented by arrow 129. In particular, the first direction 129 is a direction from the sample source towards the sampling kit 120. This approach of having a flow regulator 124 that allows unidirectional flow is effective in preventing the return of any residual sample that may remain in the first conduit 104 or a corresponding sub-conduit 116 after the sampling instance. It may be noted that the residual sample left in the conduits 104 or 116 is no longer considered as sterile media because the conduits 104 and 116 are considered to be exposed to the environment outside the sampling assembly 100 during a sampling instance as syringes are considered open devices that may be exposed to the non-sterile environment that may be present outside the sampling assembly 100. Accordingly, the use of the flow regulator 124 and the design of the sampling assembly 100 ensures that the sample flowed out of the sample source is not allowed to flow back to the sterilized environment. Hence, the systems and methods of the present specification are configured to provide provisions for aseptic sampling in a non-sterile environment.

Among other advantages of the sampling assembly of the present application it is the ease with which the sampling assembly may be constructed and easy availability of materials that are used in the sampling assembly, which are easily and readily sterilizable. In the device shown in FIG. 1, for example, the first conduit 104 and the lengths of the sub-conduits 116 which make up the first conduit 104, as well as the sub-conduits 116 ending at sub-ports 112 may be made of any suitable biologically inert material which is sufficiently rigid to maintain a liquid conduit bore therein and to permit interconnection using suitable connection devices, while at the same time being sufficiently flexible to permit bending and working as may be needed to effect connections.

It may be noted that various other embodiments of the present specification may be plausible. By way of example, the first conduit may be a t-shaped connector, where a secondary branch may have one or more sub-ports. Also, instead of a single first and second flow controller for each sub-conduit 116 and sampling kit 120, two or more first and/or second flow controllers 122 and 125 may be disposed between two sub-conduits 116, or operatively coupled to the sampling kits 120. By way of example, two first flow controllers 125 may be disposed between two sub-conduits 116 as a safety measure in the scenario where one of the first flow controllers 125 may fail to respond.

In certain embodiments, the various components of the sampling assembly 100, such as, but not limited to, the sample source, the first conduit 104, the sampling kits 120, and the like are sterilized prior to being coupled to form the sampling assembly 100. Optionally, in some embodiments, the first port 106 of the first conduit 104 which is to be arranged in liquid communication with the sample source may be closed upon initial construction. Further, the sampling assembly 100 may be sterilized by any suitable means, including irradiation since no metal parts are involved.

Figure 2:
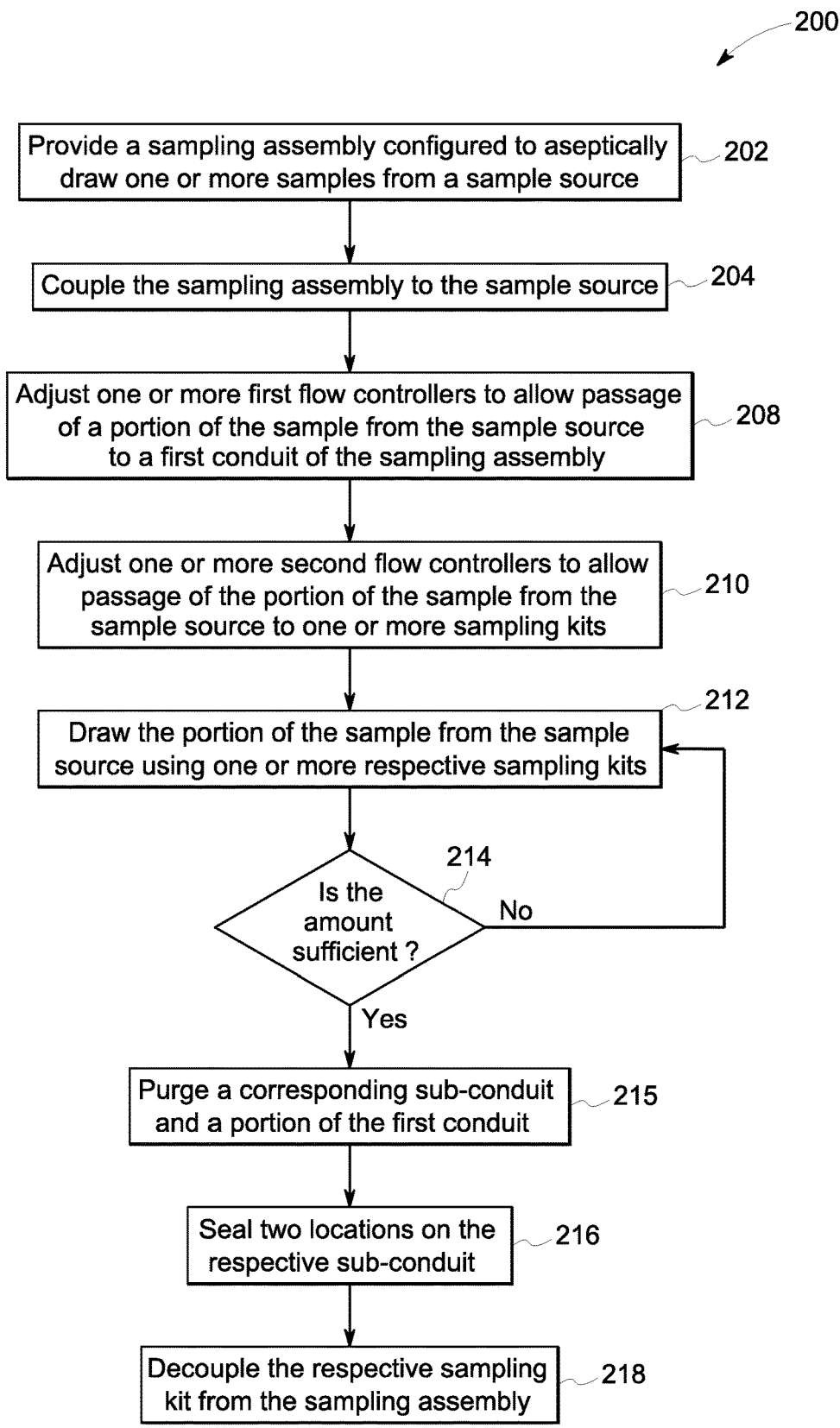
FIG. 2 is a flow chart of an exemplary method of sampling using a sampling assembly, in accordance with aspects of the present specification.

FIG. 2 is an example method 200 for using a sampling assembly of the present specification to aseptically draw a sample from a sample source at one or more instances in time. Advantageously, the method prevents introduction of contamination in the sampling assembly during or after a sampling instance. Further, the method enables time efficient and aseptic sampling at one or more instances in time. By way of example, since the sampling containers and/or sampling kits are pre-coupled to the first conduit in the sterilized pre-assembled sampling assembly, a user is not required to laboriously couple a sampling kit to the sample source for each sampling instance. It should be noted that in conventional methods where the user is required to couple the sampling kit to the sample source for each sampling instance, each sampling instance of coupling the sampling kit to the sample source is accompanied by increased likelihood of introduction of contaminants in the sample source. Accordingly, the probability of introduction of contaminants in the sample source increases drastically with the increase in the number of sampling instances. Further, the sampling assembly of the present specification which includes the plurality of sampling containers that is coupled to the first conduit and available for a plurality of sampling instances provides the advantage of carrying out the plurality of sampling instances in an aseptic fashion without introduction of contaminants in the sample source, which may otherwise occur in instances where a respective sampling kit needs to be individually coupled to the sample source at the time of sampling for each and every sampling instance.

In certain embodiments, a sample mixture having an inoculum of cells to be cultured may be introduced into a sample source, such as, but not limited to, a culture unit, a bioreactor, or any other suitable vessel. Further, a growth medium may be introduced in the sample source, for example to nourish the cells in the sample source. Further, provisions (e.g., flow controllers, flow regulators, or both) may be provided for the first conduit and/or the sampling kits such that the sampling kits and the sample source are not undesirably influenced, e.g., during the step of drawing the sample or following the step of drawings the sample.

At step 202, a sampling assembly configured to aseptically draw one or more samples from a sample source is provided. The sampling assembly is a pre-assembled sterilized arrangement that includes a first conduit and a plurality of sub-conduits. Further, the first conduit includes a first port and a second port. Additionally, each sub-conduit has a corresponding sub-port. Further, one or more sub-ports are operatively coupled to a corresponding sampling kit. The sampling kit may be sterilized before coupling the sampling kit to the corresponding sub-port.

Next, at step 204, the sampling assembly may be coupled to the sample source. In particular, a first port or one of the sub-ports may be coupled to a sample source. In one example, the first port of the first conduit may be coupled to the sample source by thermal fusion to the tube pre-attached to the culture vessel, such as a bioreactor. Alternatively, in some embodiments, the sampling assembly may be pre-attached to a sample source to form a sampling system. The sampling system may be available as a ready to use arrangement. In these embodiments, step 204 may be redundant.

At step 208, for a sampling instance, one or more first flow controllers may be adjusted to allow passage of a portion of the sample from the sample source to the first conduit. It may be noted that for the sampling kit adjacently disposed to the sample source, if the corresponding flow controller is not disposed between the sample source and the corresponding sub-conduit it may not be required to adjust the corresponding flow controller.

At step 210, one or more second flow controllers are adjusted to allow the portion of the sample from the sample source to flow into a respective sampling kit. Next, at step 212, a portion of the sample is drawn from the sample source into the first conduit, and subsequently into the sampling kit. In one embodiment, the steps 206 and 210 may be followed in same or different sequence to enable sampling. Further, for the next sample instance, one or more first flow controllers may also need to be adjusted to allow the flow of the sample from the sample source to a respective sampling kit. Further, it may be noted that in some instances, orientation of the sample source may be adjusted to allow sample to flow out of the sample source into the first conduit. In a non-limiting example where the sample is disposed in a portion of a volume of the sample source, the sample source may be tilted to allow the sample to flow to a port of the sample source that is in fluidic communication with the first conduit.

At step 214, an amount of sample collected in the sampling kit may be determined. Further, it may be noted that, at step 214 if it is determined that the amount of sample collected is sufficient or even more than a desirable amount, the orientation of the sample source may be re-adjusted to prevent any further sample from flowing from the sample source into the first conduit.

At step 215, if the amount of the sample collected in the sampling kit is sufficient or more than sufficient, the corresponding sub-conduit and the associated portion of the first conduit are purged by drawing the remaining sample from the sub-conduit and the portion of the first conduit into the sampling kit which is being used to collect the sample for that particular sampling instance. In one example, while purging, the orientation of the sample source may be returned to the original orientation that existed prior to the sampling instance. Consequently, this way only the portion of the sample present in the first conduit and the sub-conduit will be drawn into the sampling kit, and the fresh sample from the sample source will not be drawn in the sampling kit. Advantageously, this drawing of the sample disposed in the portion of the first conduit and the corresponding sub-conduit facilitates purging of the portion of the first conduit. Accordingly, during a subsequent sampling instance, the chances of a detectable amount of sample being carried over from this previous sampling instance into the next sampling instance is reduced drastically. Additionally, use of the flow regulator prevents the sample that has flown out of the sample source and into the first conduit from going back into the first conduit, thereby, retaining the sterility of the sample in the sample source.

After purging, at step 216, one or more locations on the corresponding sub-conduit may be hermetically sealed. At step 218, the sampling kit may be decoupled from the sampling assembly by disengaging a portion of the sub-conduit from the sample assembly by cutting the sub-conduit between the two sealed locations. Sealing the sub-conduit at two locations before disengaging helps in preventing introduction of any contaminants from the open end formed because of decoupling of the sampling kit.

With returning reference to step 214, if at step 214 it is determined that the quantity of the sample collected in the sampling kit is not adequate and is less than the desirable amount, some more amount of sample may be drawn from the sample source (step 212). And steps 212 and 214 may be repeated accordingly. In one example, additional sample may be drawn by further pulling a syringe to increase a volume in a barrel of the syringe to accommodate additional amount of sample. Further, more sampling instances may be performed as and when desirable or until all the sub-ports, respective sub-conduits and respective sampling kits are utilized. In a particular embodiment, the sampling may be performed in a sequential order in the direction starting from the sample source and travelling towards the second port.

Figure 3:
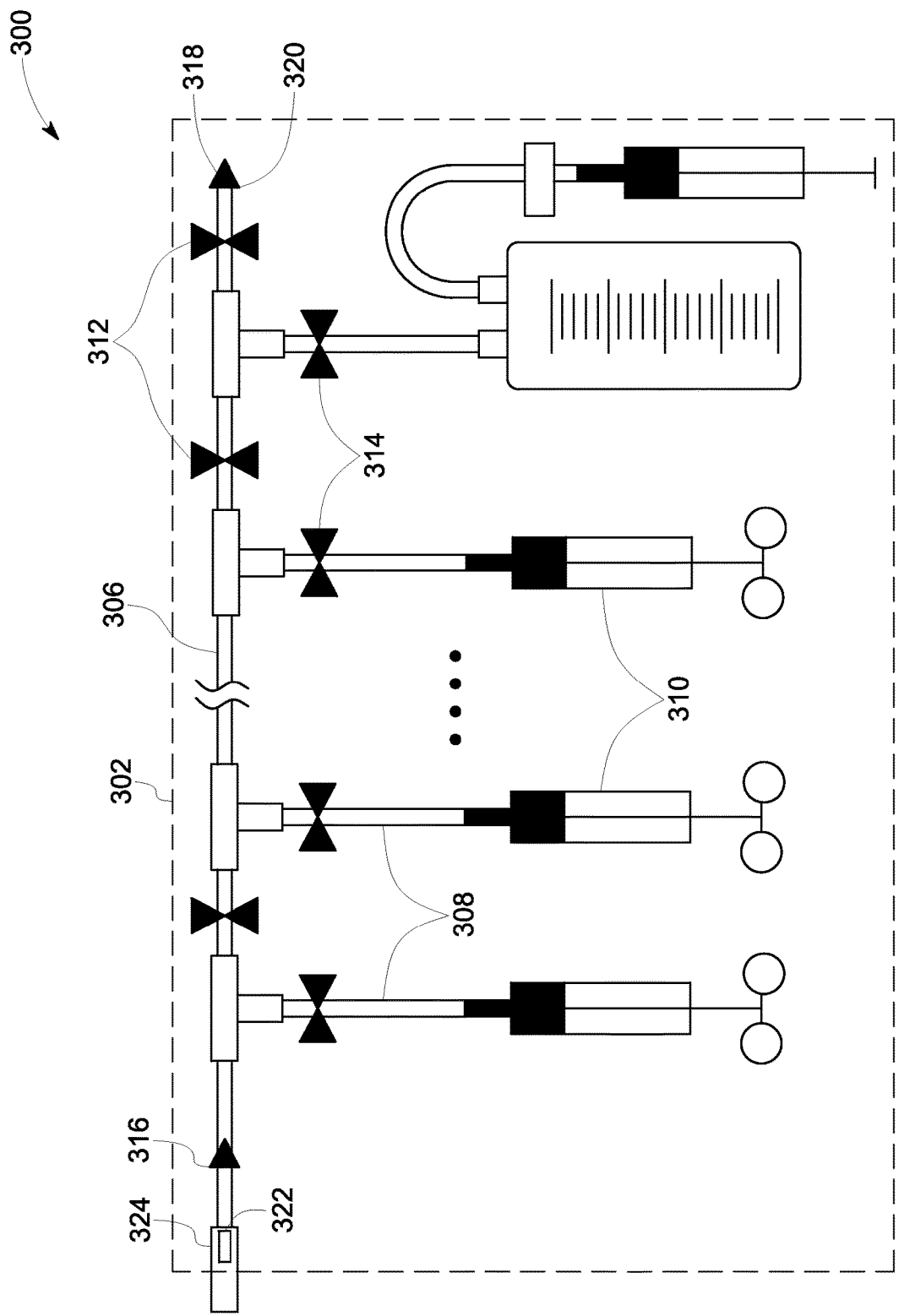
FIGS. 3-7 are schematic representations of steps involved in the method of sampling using a sampling assembly, in accordance with aspects of the present specification.

FIGS. 3-7 illustrate steps involved in a sampling instance using a sampling assembly 300 of the present specification. By way of example, FIGS. 3-7 may be considered as schematic representations of steps involved in the method of sampling of FIG. 2. FIG. 3 represents a schematic view of a sampling system 300 having a sampling assembly 302 operatively coupled to a sample source 304 (see FIG. 4) having a biological inoculum 305. The sampling system 300 is configured to enable aseptically drawing one or more samples at one or more instances in time. The sample source 304 includes an outlet port 307. In one example, the sample source 304 may be a culture vessel, such as a bioreactor, a fermentor, or any other suitable culture vessel. In the illustrated embodiment, the sample assembly 302 includes a first conduit 306, a plurality of sub-conduits 308, and a plurality of sampling kits 310 coupled to the first conduit 306 via the sub-conduits 308. Further, the sampling assembly 302 also includes a plurality of first flow controllers 312, a plurality of second flow controllers 314 and one or more flow regulators 316. The first conduit 306 includes a first port 322 and a second port 320. Further, a mechanical stopper 318 may be used to hermetically seal the first port 322 of the first conduit 306. In instances where the sampling assembly 302 is available as a stand-alone ready to use arrangement, the first port 322 of the first conduit 306 is hermetically sealed. In a non-limiting example, a removable seal 324 may be used to hermetically seal the sampling assembly 302. In one embodiment, the sampling assembly 302 may be aseptically attached to the sample source 304 at the point of use using known techniques, such as tube fusion. Further, the seal 324 at the first port 322 may be removed immediately before coupling the first port 322 of the sampling assembly 302 to the outlet port 307 of the sample source 304 to provide a fluidic communication between the sample source 304 and the first conduit 306. In other instances where the sampling assembly 302 is pre-attached to the sample source 304 to form the sampling system 300, the sampling system 300 may be available as a single integrated unit that is ready to use. In both instances, in operation, the first port 322 is coupled to the outlet port 307 of the sample source 304. It may be noted that the sampling assembly 302 or the sampling system 300 is a pre-assembled and sterilized arrangement that is pre-fitted with sampling kits 310.

Figure 4:
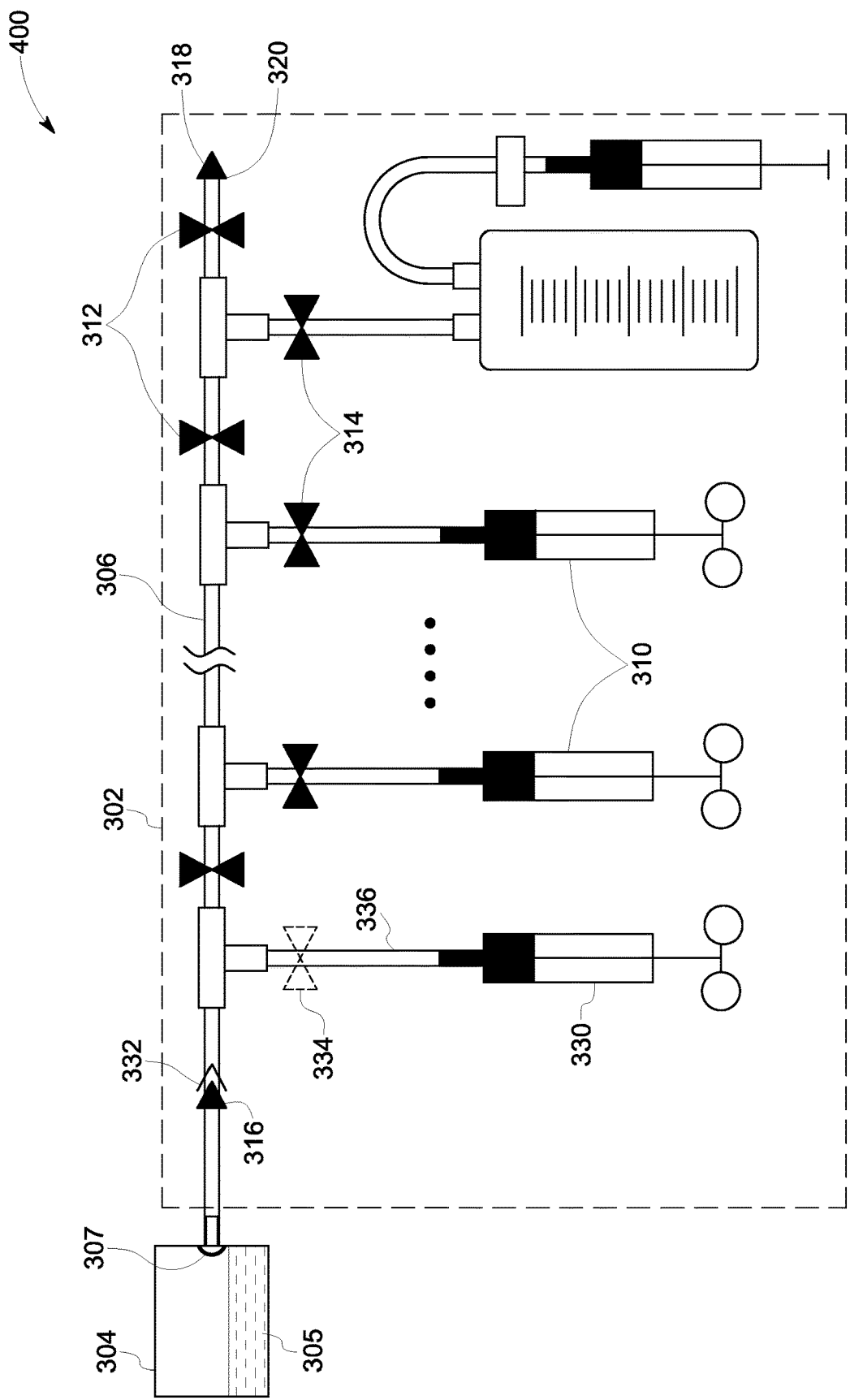

Further, as illustrated in the representation 400 of FIG. 4, a portion of the inoculum 305, also referred to as a sample 338 (see FIG. 5), may be drawn in the first conduit 306 and subsequently in the sub-conduit 336 using the flow regulator 316. Advantageously, the flow regulator 316 allows unidirectional flow of the inoculum 305 in a direction from the sample source 304 to the first conduit 306, as represented by arrow 332. Further, a respective flow controller 334 of the plurality of second flow controllers 314 is adjusted to allow the sample 338 to flow into the corresponding sub-conduit 336 of the plurality of sub-conduits 308. Further, the flow controller 334 of the plurality of first flow controllers 312 may be maintained in an open position during sampling using a syringe 330 to allow flow of the sample to the syringe 330. Also, it may be noted that in general, initially (before starting of the sampling instance) the corresponding flow controllers 312 and 314 may be maintained in a closed position.

Figure 5:
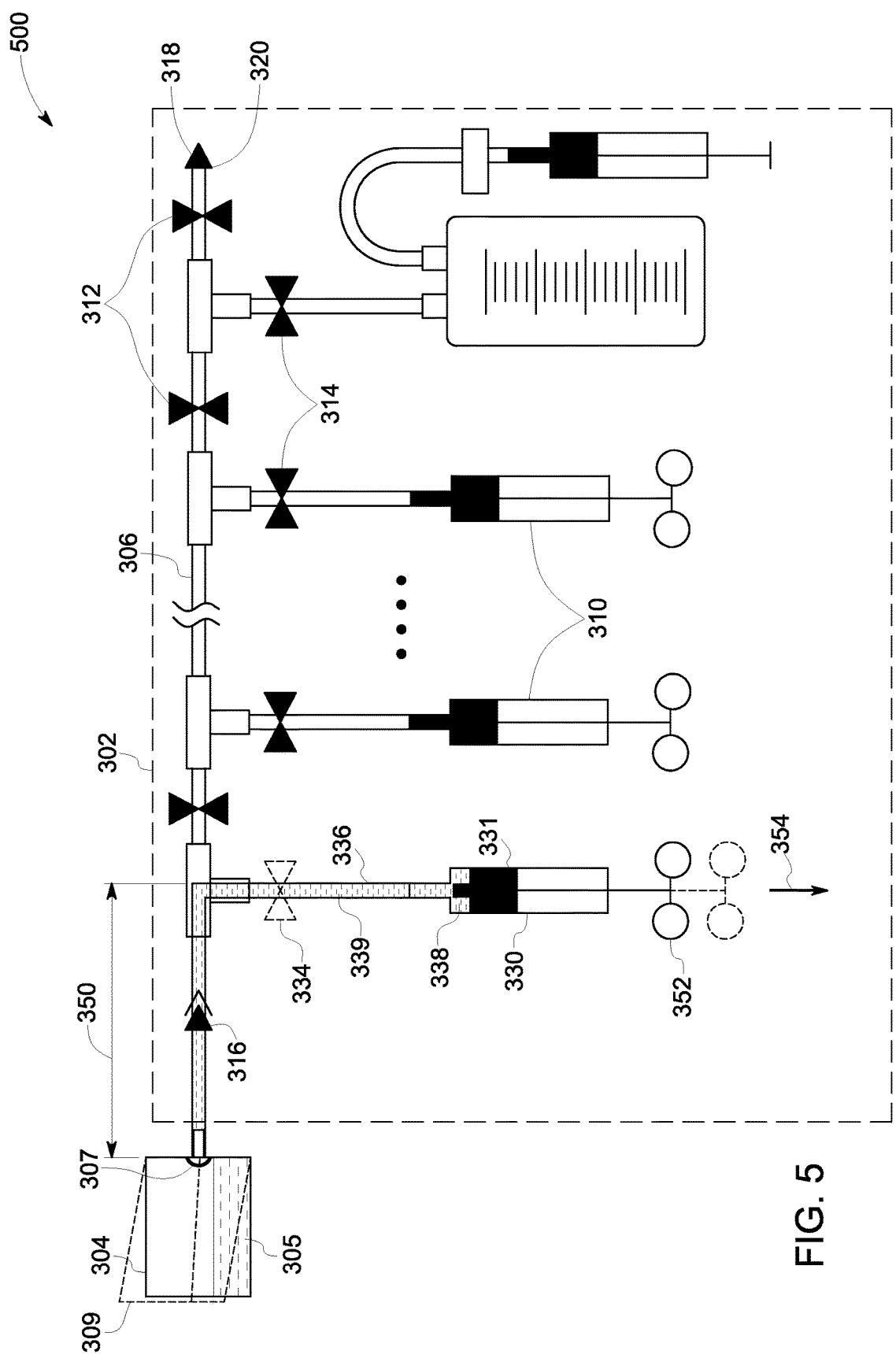

Further, as illustrated in the schematic view 500 of FIG. 5, the sample 338 may be drawn into a portion 350 of the first conduit 306 and the sub-conduit 336 using negative pressure that may be generated at least in part in a barrel 331 of the syringe 330 while the flow controller 334 is maintained in an open position to allow fluidic communication between the sample source 304 and the syringe 330. In the illustrated embodiment, as represented by the dashed line 309, the sample may be drawn by tilting the sample source 304 such that the inoculum is accessible to the first conduit 306 via the outlet port 307 of the sample source 304. Moreover, the sample 338 may be continued to be drawn into the syringe 330 by increasing the negative pressure by pulling a syringe head 352 further in the direction represented by arrow 354. In a specific example, the negative pressure in the barrel 331 of the syringe 330 may be generated by pulling the syringe 330 approximately half way in a direction represented by arrow 354 to draw a desirable amount of sample 338 in the syringe 330.

Further, after the desirable amount of the sample 338 is collected in the syringe 330, some amount of sample may still remain in the tubing (portion 350 of the first conduit 306 and the sub-conduit 336) between the sample source 304 and the syringe 310. This sample may be referred to as a residual sample 339. The residual sample, if not removed from the tubing, may be carried over in the next sampling instance. Accordingly, the sampling assembly 302 may be purged after each sampling instance to remove the residual sample 339 from the associated tubing for that particular sampling instance.

Figure 6:
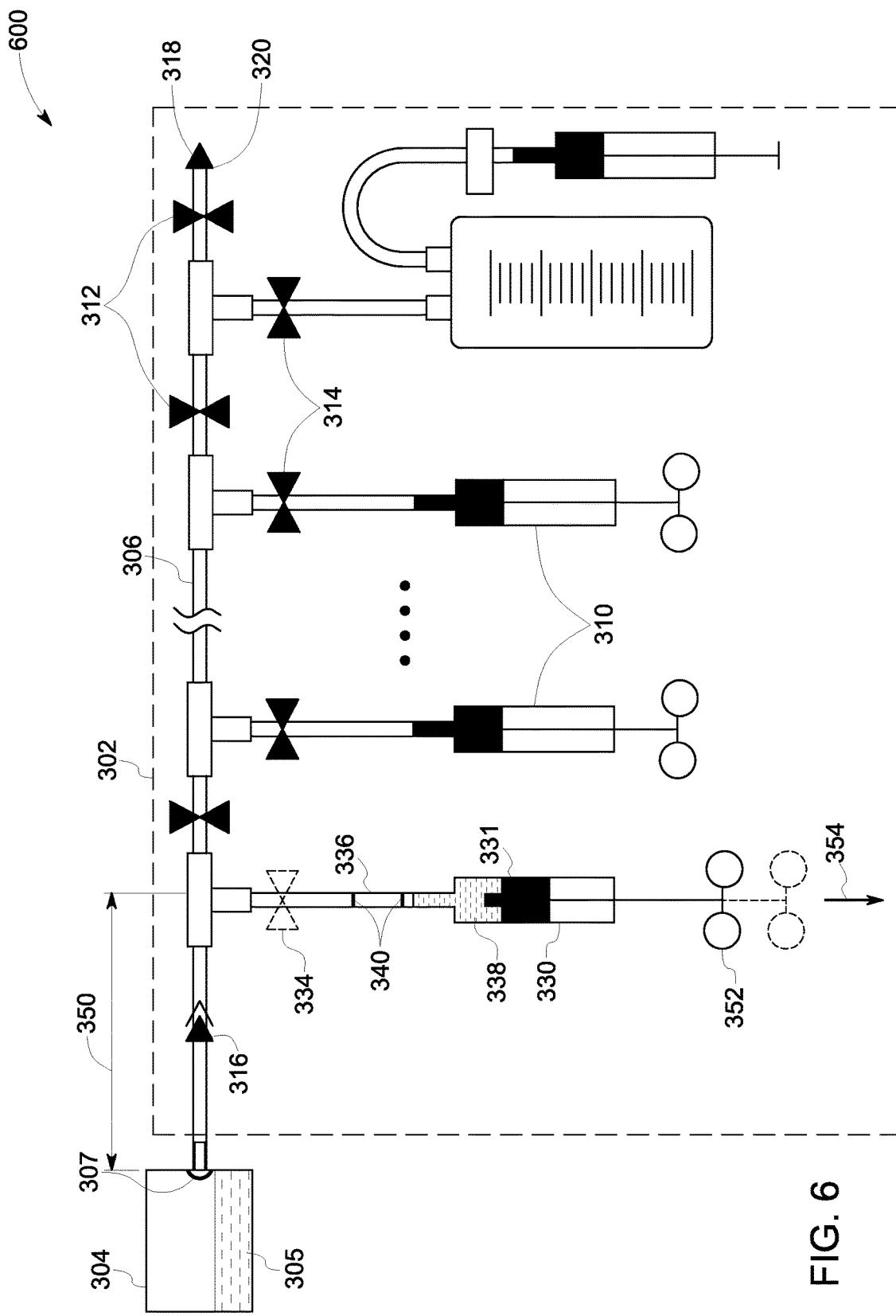

Turning now to FIG. 6, if the desirable amount or even more than the desirable amount of the sample 338 is collected in the syringe 330, the sampling assembly 302 may be purged. Further, for purging the sampling assembly 302, fluidic communication between the sample source 304 and the first conduit 306 is discontinued. In a particular example, the fluidic communication between the inoculum 305 and the first conduit 306 may be discontinued by ensuring that the outlet port 307 of the sample source 304 is not in accessible to the inoculum 305. Next, as shown in the schematic representation 600 of FIG. 6, the syringe 330 is pulled further in the direction 354 to purge the portion of the first conduit and the corresponding sub-conduit 336 by drawing the residual sample 339 (see FIG. 5) in the syringe 330. Further, the sub-conduit 336 is sealed at two locations 340. In a non-limiting example, the sub-conduit 336 may be sealed at the two locations 340 using bar sealers.

Figure 7:
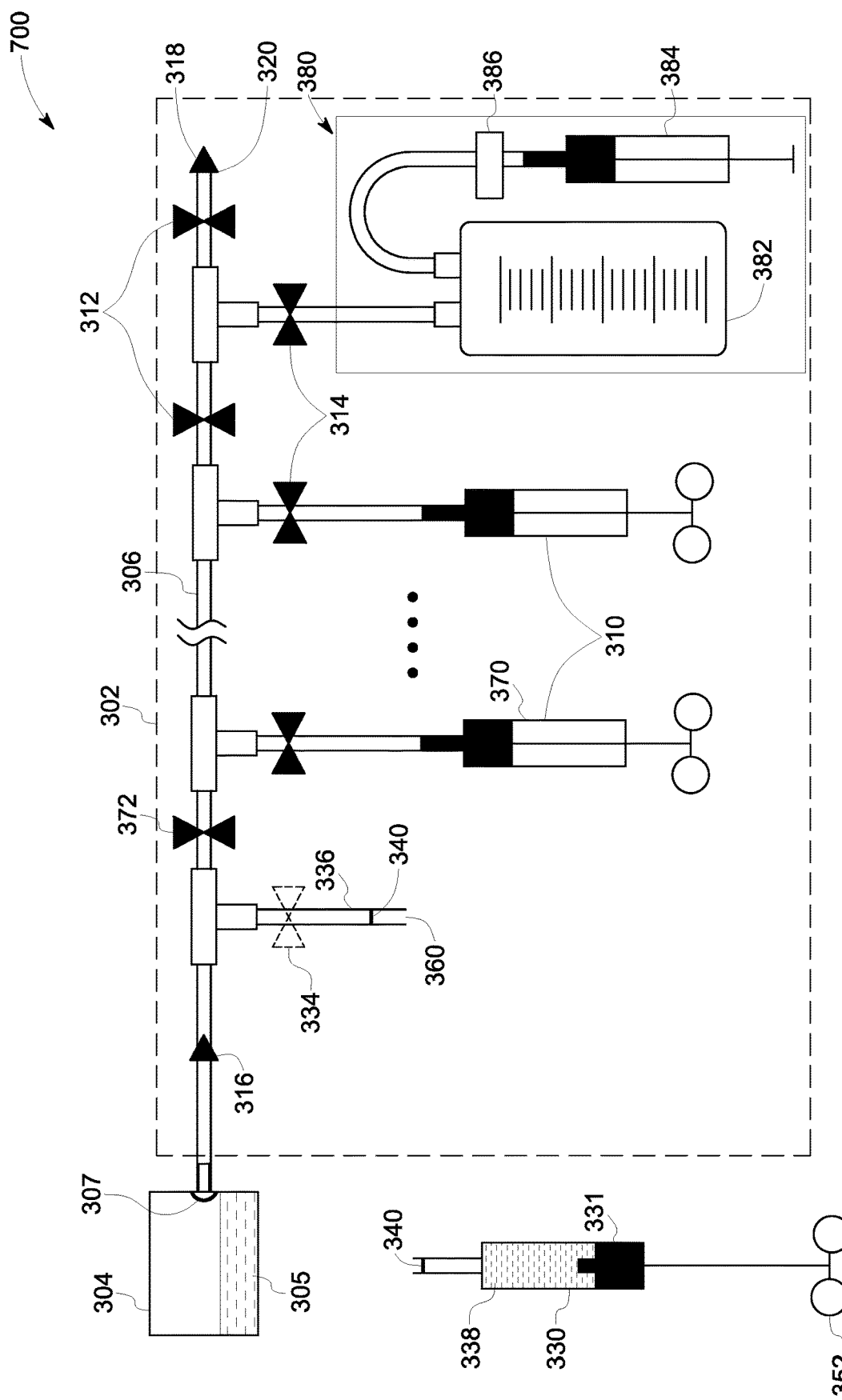

Referring now to FIG. 7, as illustrated in the schematic representation 700, the sampling instance for the syringe 330 is concluded by decoupling the syringe 330 from the sampling assembly 302 by cutting the sub-conduit 336 at a location 360 disposed between the locations 340. With the locations 340 being sealed, the syringe 330 as well as the sub-assembly 302 are hermetically sealed when the sub-conduit is cut at the location 360.

It may be noted that in case of a subsequent sampling instance, where a sampling kit 370 is used to draw a sample, a first flow controller 372 of the plurality of first flow controllers 312 may be adjusted to allow a flow of the sample from the sample source 304 towards the sampling kit 370. Moreover, in a sampling instance, a sampling kit 380 may be used to draw a larger sample. In the illustrated embodiment, the sampling kit 380 includes a sampling container 382, a syringe 384 and an air filter 386. The air filter 386 is disposed between the sampling container 382 and the syringe 384, so as to prevent contaminants from the surrounding environment from entering in the sampling container. Further, the sampling container 382 may be used when a greater volume of sample is desirable.

Advantageously, the assemblies, systems and methods of the present specification enable effective withdrawal of a sample from a sterile sample source in an aseptic, rapid and cost-effective manner. Further, since the sampling assembly is pre-assembled and sterilized, the sampling assembly and the sampling process of the present specification permits a plurality of sampling instances whereby the sterile environment is safeguarded.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A sampling assembly configured to be coupled to a sample source, wherein the sampling assembly is configured to facilitate aseptic sampling at one or more instances in time, comprising:

a first conduit comprising a first port and a second port, wherein the first port is configured to be coupled to the sample source, wherein the second port is a functionally closed end, and wherein the functionally closed end is hermetically sealed;
a plurality of sub-conduits having corresponding sub-ports, wherein each of the plurality of sub-conduits is operatively coupled to the first conduit at a respective connector junction, wherein the sub-ports are disposed between the first port and the functionally closed end of the first conduit, and wherein each of the sub-ports is in fluidic communication with the first conduit;

a plurality of sampling kits, wherein each sampling kit of the plurality of sampling kits is operatively connected to a respective sub-port of a corresponding sub-conduit and configured to provide negative pressure to facilitate the flow of a portion of the sample from the sample source into the sampling kit; and a check valve operatively coupled to the sample source for a unidirectional flow of at least a portion of a sample from the sample source to the plurality of sampling kits in a first direction, wherein the first direction is a direction from the sample source towards the plurality of sampling kits.

2. The sampling assembly of claim 1, wherein the first conduit is a continuous conduit.

3. The sampling assembly of claim 1, wherein the plurality of sub-conduits emanates from spaced-apart areas along the first direction.

4. The sampling assembly of claim 1, wherein one or more sampling kits of the plurality of sampling kits comprise a syringe, a sampling container, an air filter, or combinations thereof.

5. The sampling assembly of claim 1, further comprising a plurality of first flow controllers operatively coupled to one or more sub-conduits of the plurality of sub-conduits.

6. The sampling assembly of claim 1, further comprising a plurality of second flow controllers operatively coupled to one or more sampling kits of the plurality of sampling kits.

7. The sampling assembly of claim 1, wherein the check valve is disposed between the sample source and a connector junction disposed closest to the sample source.

8. The sampling assembly of claim 1, wherein the functionally closed end is clamped, thermally sealed, or a combination thereof.

9. A sampling system configured to facilitate aseptic sampling at one or more instances in time, the sampling system comprising:

a sample source configured to house a biological inoculum;

a sampling assembly, comprising:

a first conduit comprising a first port and a second port, wherein the first port is configured to be coupled to the sample source, wherein the second port is a functionally closed end, and wherein the functionally closed end is hermetically sealed;

a plurality of sub-conduits having corresponding sub-ports, wherein each of the plurality of sub-conduits is operatively coupled to the first conduit at a respective connector junction, wherein the sub-ports are disposed between the first port and the functionally closed end of the first conduit, and wherein each of the sub-ports is in fluidic communication with the first conduit;

a plurality of sampling kits, wherein each sampling kit of the plurality of sampling kits is operatively connected to a respective sub-port of a corresponding sub-conduit and configured to provide negative pressure to facilitate the flow of a portion of the sample from the sample source into the sampling kit; and a check valve operatively coupled to the sample source for a unidirectional flow of at least a portion of the biological inoculum from the sample source to the plurality of sampling kits in a first direction, wherein the first direction is a direction from the sample source towards the plurality of sampling kits.

10. The sampling system of claim 9, wherein the check valve is disposed between the sample source and a connector junction disposed closest to the sample source.

11. The sampling system of claim 9, further comprising a mechanical stopper disposed at the functionally closed end of the first conduit.

12. The sampling system of claim 9, wherein at least one sampling kit of the plurality of sampling kits comprises a syringe.

13. The sampling system of claim 9, wherein at least one sampling kit of the plurality of sampling kits comprises a sampling container operatively coupled to a corresponding sub-port.

14. The sampling system of claim 13, wherein one or more of the plurality of sampling kits comprise a syringe operatively coupled to the sampling container.

15. A sampling assembly configured to be coupled to a sample source, wherein the sampling assembly is configured to facilitate aseptic sampling at one or more instances in time, the sampling assembly comprising:

a first conduit comprising a first port and a second port, wherein the first port is configured to be coupled to the sample source, wherein the second port is a functionally closed end, and wherein the functionally closed end is hermetically sealed;

a plurality of sub-conduits having corresponding sub-ports, wherein each of the plurality of sub-conduits is operatively coupled to the first conduit at a respective connector junction, wherein the sub-ports are disposed between the first port and the functionally closed end of the first conduit, and wherein each of the sub-ports is in fluidic communication with the first conduit;

a plurality of sampling kits, wherein each sampling kit of the plurality of sampling kits is operatively connected to a respective sub-port of a corresponding sub-conduit and configured to provide negative pressure to facilitate the flow of a portion of the sample from the sample source into the sampling kit, and wherein at least one of the plurality of sampling kits comprises a syringe coupled to a sampling container; and a flow regulator operatively coupled to the sample source for a unidirectional flow of at least a portion of a sample from the sample source to the plurality of sampling kits in a first direction, wherein the first direction is a direction from the sample source towards the plurality of sampling kits.

16. The sampling assembly of claim 15, wherein the flow regulator is a check valve.

17. The sampling assembly of claim 15, wherein the at least one of the plurality of sampling kits further comprises an air filter coupled to the sampling container and the syringe, and wherein the air filter is disposed between the sampling container and the syringe.

18. The sampling assembly of claim 15, further comprising a mechanical stopper disposed at the functionally closed end of the first conduit.

* * * * *